United States Patent [19]

Kono et al.

[11] Patent Number: 4,851,153

[45] Date of Patent: Jul. 25, 1989

[54] CONDUCTIVE HIGH MOLECULAR WEIGHT COMPOSITION

[75] Inventors: Masanao Kono; Yoshihiro Hasegawa, both of Kakogawa; Yasutaka Nishi, Takasago; Yasuyoshi Sanada, Kakogawa; Tatsuji Mizuta, Kobe; Ryo Inoue, Himeji; Shinsuke Ohara, Kyoto, all of Japan

[73] Assignee: Harima Chemicals, Inc., Hyogo, Japan

[21] Appl. No.: 51,524

[22] Filed: May 19, 1987

[30] Foreign Application Priority Data

May 19, 1986 [JP] Japan .................. 61-114442
Jun. 30, 1986 [JP] Japan .................. 61-154812

[51] Int. Cl.$^4$ .............................. H01B 1/20
[52] U.S. Cl. ................... 252/518; 428/420; 428/901; 524/394; 524/396; 524/398; 524/399; 524/400
[58] Field of Search ............... 252/518; 524/394, 396, 524/398, 399, 400; 428/420, 901

[56] References Cited

U.S. PATENT DOCUMENTS

| | | | |
|---|---|---|---|
| 2,960,490 | 11/1960 | Hinkes | 524/394 |
| 3,978,378 | 8/1976 | Tigner et al. | 428/704 |
| 4,490,283 | 12/1984 | Kleiner | 524/439 |
| 4,510,078 | 4/1985 | Mehta | 252/510 |

*Primary Examiner*—Robert A. Wax
*Attorney, Agent, or Firm*—Birch, Stewart, Kolasch & Birch

[57] ABSTRACT

A conductive high molecular composition which comprises a non-conductive polymer component incorporated with a metal salt, characterized in that the melt salt is a salt of a metal with an acid substance selected from an organic carboxylic acid, rosin and a rosin derivative. This composition has an insulating property in the normal state but functions as an electroconductive material only in the event it is interposed between slightly spaced metals and heated. Thus, the composition can be used not only as an insulating binder but also for imparting conductivity only in the desired spots of electronic parts, keeping the other areas of the parts electrically insulated. The composition thus possessing a specific dual function is particularly useful in the electronic industry field.

5 Claims, No Drawings

CONDUCTIVE HIGH MOLECULAR WEIGHT COMPOSITION

BACKGROUND OF THE INVENTION

1. Field of the Invention

The present invention relates to a conductive high molecular composition useful for the manufacture of electronic circuits. More particularly, the present invention relates to a conductive high molecular composition comprised of a high molecular weight substance incorporated with a specific metal salt, which has an insulating property in the normal state but functions as an electroconductive material only in the event it is interposed between slightly spaced metal films and heated.

2. Description of the Prior Art

What is carried out from the past for the formation of electronic circuits is to bond electronic parts to circuit substrates or to laminate such circuit substrates to form multilayer integrated circuits. Generally adopted for bonding one circuit substrate to the other or electronic parts to such circuit substrates is a method wherein the surfaces of the metal films on the individual circuit substrates or electronic parts are bonded with a solder. A pasty solder is usually employed for soldering a number of minute spots in an efficient and precise manner.

A conventional pasty solder is in the form of a pasty dispersion of a powder of a soldering alloy such as a tin-lead alloy and a flux in a high boiling point solvent such as a mineral spirit functioning as a viscosity-regulating vehicle. The use of such pasty solder for forming an electronic circuit on a substrate metal of a circuit panel generally necessitates the steps of applying the pasty solder in a given configuration onto the surface of a panel having electronic parts thereon by way of screen printing or by the aid of a dispenser and heating the panel to melt the powder of the soldering alloy dispersed in the pasty solder and attaching it onto the surface of the substrate metal by a cooperative action of the flux. When the pasty solder is heated, the powder of the soldering alloy is molten and any oxide existing on the surface thereof is reduced by the action of the flux to form pure molten soldering alloy particles having a clean surface. At the same time, the substrate metal on the panel is also reduced to have a clean surface. Thus, the molten soldering alloy particles are improved in their coagulating force and wettability for the substrate metal, and as a result, a film of the soldering alloy is formed on the surface of the substrate metal.

In such a pasty solder, the soldering alloy exists in the form of discrete free alloy particles separated from the flux and the solvent. The size of the particles may be very small but is still too large to form a homogeneous composition together with the flux and the solvent. Many attempts are still being made to minimize the size of the alloy particles but the size is substantially limited at present to about 10μ in diameter. The alloy particles should have a diameter less than 1μ to form a stable homogeneous pasty solder.

In recent years, the density of the printed circuits for electronic equipment became higher so that the circuit patterns on substrates are constructed by a number of extremely thin lines. In some cases, printed circuits are constructed by a circuit pattern having lines of several hundred microns in width at similar intervals. As the density of circuit patterns becomes higher, therefore, a pasty solder therefor should be supplied in a more precise manner. In case a pasty solder is supplied by way of screen printing for the manufacture of such high density printed circuits, a screen having a smaller mesh should be used. In case a dispenser is used for supplying a pasty solder, the use of an extrusion nozzle having a smaller diameter becomes necessary as well. Since solid particles of the soldering alloy are contained in the pasty solder as described above, however, the size of the particles cannot eventually be disregarded at the time of supplying the pasty solder to substrates by way of screen printing or by the aid of a dispenser. In case of supplying a pasty solder by way of screen printing, solid particles of the soldering alloy contained therein often cause clogging of the screen so that it becomes difficult to supply the alloy particles homogeneously in a given configuration. Further, friction between the alloy particles and the screen may cause damage of a mask, thus making the life of the screen short. In case of using a dispenser for the supply of a pasty solder, the alloy particles clog the extrusion nozzle of the dispenser whereby the clogging particles function as a filter for the pasty solder passing through the nozzle to permit passage of only the flux and the solvent while leaving the solid particles of the soldering alloy, thus making it extremely difficult to extrude the pasty solder wherein the alloy particles are homogeneously dispersed.

Soldering between the alloy particles and the substrate metal is attained, as described previously, by mutual coagulation force and enhanced substrate metal-wetting property of the molten alloy particles. Since surface tension of the individual molten alloy particles is strong, however, it is difficult to allow all of the alloy particles to participate in soldering. The alloy particles not participating in soldering remain on the substrate panel and cause occurence of unexpected short circuits between the lines of the circuit pattern. Thus, a short circuit may easily be formed by existence of even a single alloy particle between the lines constituting the circuits, thus resulting in a detrimental defect. To avoid such result, it is recommended to wash the printed circuits after soldering with an organic solvent for eliminating any residual alloy particle. Even by such washing, it is difficult to eliminate residual alloy particles entirely from the treated circuits.

Such a drawback may be overcome more or less by reducing the diameter of the particles of the soldering alloy used. However, the reduction in the diameter of the particles makes the production cost higher and the particles in the resultant pasty solder so stable that coagulation of the alloy particles may hardly occur and makes the soldering operation itself difficult.

Besides the methods above mentioned for using a pasty solder to form a metal film on the desired areas of circuit substrates, the use of an electroconductive polymeric substance comprised of a metal powder dispersed in a polymeric substance as a matrix is also known in this art for imparting electroconductivity to electric parts. From the past, there is widely known a conductive high molecular composition which is comprised of a polymeric substance such as rubber or a synthetic resin having been incorporated with a powdery conductive material such as a metal or alloy powder or carbon to provide the polymeric substance with conductivity. However, a conductive high molecular composition of such type can not be used for treating circuit substrates therewith, since such composition itself is electroconductive and will make all the metal parts on circuit substrates electroconductive when interposed between the circuit substrates.

The above mentioned various drawbacks and disadvantages of the conventional pasty solder and conductive high molecular compositions result apparently from their metal-liquid or metal-solid two heterogenous phase compositions wherein metal particles are dispersed in an organic liquid or solid medium and also from their electroconductivity in the normal state because of free metal particles contained in the compositions.

In case of using a substance for attaching electronic parts to circuit substrates or bonding such circuit substrates mutually, the substance to be used for such purpose should be of insulating property but should impart conductivity only to the desired spots of the circuit substrates. In the field of the electronic industry, therefore, there is room for making remarkable improvements in the conventional pasty solder and conductive high molecular compositions, especially in their chemical composition, in the case of using them for the above purpose. Thus, there is a strong demand for developing a new type conductive composition for treating circuit substrates without the above mentioned drawbacks.

BRIEF SUMMARY OF THE INVENTION

Accordingly, it is an object of the present invention to provide a new conductive high molecular composition for treating circuit substrates, which overcomes the various drawbacks seen in the case of using the conventional pasty solders or conductive high molecular compositions.

It is another object of the present invention to provide a conductive high molecular composition which has an electrically insulating property in the normal state but imparts conductivity only to the desired spots of the objects treated therewith under heating.

It is still another object of the present invention to provide a conductive high molecular composition comprising a specific metal salt dispersed in a polymeric substance and being free of any metal particles.

It is further object of the present invention to provide a conductive high molecular composition utilizable for bonding circuit substrates while keeping electronic parts thereon insulated but making conductive only those slightly spaced from each other on the bonded substrates.

Other and further objects, features and advantages of the present invention will become apparant more fully from the following description.

As a result of extensive research made for developing a new conductive high molecular composition for treating circuit substrates, it has now been found that all the drawbacks and disadvantages seen in the conventional pasty solders and conductive high molecular compositions having metal particles dispersed therein can be overcome by incorporating a specific metal salt into a polymeric non-electroconductive material.

In accordance with the present invention, there is provided a conductive high molecular weight composition which comprises a non-conductive polymer component incorporated with a metal salt, characterized in that the metal salt is a salt of a metal with an acid substance selected from an organic carboxylic acid, rosin and a rosin derivative.

The conductive high molecular weight composition of the present invention useful for the treatment of circuit substrates has various features as compared with the conventional similar compositions wherein free metal particles are used. One of features of the composition of this invention resides in its specific dual function; the composition is comprised of a non-electroconductive polymeric substance free of metal particles and so functions as an insulator in the normal state but functions as a conductor when it is interposed, for example, between metal films slightly spaced from each other and subjected to heat treatment. Another feature resides in the use of a specific acidic substance for the preparation of a salt of a metal therewith. Further feature resides in the relation between the metal of the metal salt and the metal on the circuit substrates. The metal for the metal salt and the metal on the circuit substrate have to be selected in such manner that the latter metal on the substrate is greater in ionization tendency than the first metal constituting the metal salt.

DETAILED DESCRIPTION OF THE INVENTION

In the composition of this invention, the acidic substances which form salts with the metals capable of functioning as conductors are selected from organic carboxylic acids preferably with at least 4 carbon atoms. As the organic carboxylic acids, the following various groups of carboxylic acids come into question: mono-, di- and polycarboxylic acids of aliphatic nature and mono-, di- and polycarboxylic acids of aromatic nature. Among the carboxylic acids of aliphatic nature, higher fatty acids and dicarboxylic acids are preferable. Illustrative of such preferable fatty acids and dicarboxylic acid are, for example, capric acid, lauric acid, palmitic acid, stearic acid, oleic acid, neodecanoic acid, sebacic acid, fumaric acid and maleic acid. The use of a higher fatty acid is more preferable. A variety of aromatic mono-, di- and tricarboxylic acids can be used for the present invention, but the use of benzoic acid, phthalic acid, isophthalic acid, trimellitic acid, pyromellitic acid and the like are preferable. Aromatic carboxylic acids contained in natural sources, such as d-pimaric acid, abietic acid and naphthenic acid can also be used preferably for the present invention. Many other organic carboxylic acids not mentioned herein can also be selected for use in the present invention so far as they can form a salt with the metal and the resultant salt attains the purpose of this invention.

In addition to these organic carboxylic acids which are commercially available, an acidic substance of natural origin containing abietic acid and d-pimaric acid can also be used for the preparation of the metal salts. Preferable examples of such natural substances are rosin and derivatives thereof. These substances are used widely as a flux for soldering from the past and contain the above mentioned acids as their predominant acidic ingredients. Illustrative of preferable rosin derivatives are, for example, disproportioned rosin, hydrogenated rosin, gum rosin, tall oil rosin and wood rosin. Further, chemically modified rosins can also be used equivalently for the preparation of the metal salts. Abietic acid and d-pimaric acid contained in natural rosin and derivatives thereof have only one carboxyl group in the molecule to be bound with the metal. In case of using rosin for the preparation of salts with a divalent or polyvalent metal such as tin, the content of the metal in the resultant salt becomes lower. Thus, rosin may be modified chemically to have plural carboxyl groups by introducing thereinto one or two carboxyl groups by way of addition reaction with a carboxylic acid. Preferable examples of the carboxylic acid to be introduced into rosin by addition reaction include maleic acid and fumaric acid. An adduct obtained, for example, by addition reaction of maleic acid to rosin have three carboxyl groups in the molecule and can be bound with the metal in an amount sufficient enough for functioning as a conductor, for example, between the metal films.

The metal capable of forming a salt with the above mentioned organic carboxylic acid, rosin or a derivative thereof (including the chemically modified rosin) is selected as a metal to be formed as a conductor on the surface of a metal (substrate metal) constituting electronic parts on a circuit. Thus, the metal is selected according to the intended use of the conductor formed on the substrate metal. In case of forming a soldering metal between the surfaces of the circuits, tin and lead are used optionally with other cooperative alloy components such as bismuth in a given proportion. In case of forming a silver conductor, silver is selected as the metal. Illustrative of the metal for forming a salt with the acid substance are, for example, zinc, cadmium, chromium, iron, nickel, cobalt, tin, lead, bismuth, copper, silver and gold. Many other metals not mentioned herein can also be used according to the intended purpose so far as they form a salt with the acidic substance.

Salts of the metal with the above mentioned carboxylic acid, rosin or a derivative thereof can be prepared according to wet and dry processes. According to the wet process, the carboxylic acid, rosin or a derivative thereof is first reacted (or neutralized) in an aqueous medium with a caustic alkali such as potassium or sodium hydroxide at room temperature or a slightly elevated temperature to form an aqueous solution on an alkali metal salt thereof. The resultant aqueous solution of the alkali metal is then reacted as such (without once isolating the solid alkali metal salt) with an aqueous solution of a salt of the metal at room temperature or a slightly elevated temperature whereby a double decomposition reaction takes place, yielding an aqueous solution of the desired salt of the metal with the carboxylic acid or rosin or a derivative thereof including an alkali metal salt as by product. The metal salt can be isolated from this aqueous solution by removing water therefrom until dryness, extracting the residue with an aromatic solvent such as toluene or xylene for the separation of the alkali metal salt, and concentrating the extract until dryness. In this wet process, a water-soluble salt of the metal used as the reactant is preferably derived from a strong or relatively strong acid for the double decomposition reaction. Examples of suitable strong or relatively strong acids include hydrohalic acids, especially hydrochloric acid, nitric acid and acetic acid. Sulfuric acid is also suitable if a salt derived therefrom is water-soluble. In case two or more metals are to be formed as an alloy on the surface of the substrate, the corresponding two or more metal salts are used for the double decomposition reaction. In this case, these metal salts may be supplied to the reaction system as a double or mixed salt or as a mixture of the individual salts which have been prepared separately and mixed in a given ratio. The use of a mixture of the individual salts is preferable since the bonding strength of the resultant product becomes greater and since the ratio of the metals can freely be varied according to the intended use.

Preferable examples of the metal salts used for the wet process (double decomposition method) include chlorides for zinc, cadmium, iron, nickel, cobalt, tin (stannous) and copper; sulfates for zinc, cadmium, iron, nickel, cobalt and copper; nitrates for zinc, cadmium, nickel, cobalt, copper and silver; and acetates for zinc and lead. In case of forming a solder film between the metal surfaces of the laminated circuit substrates, a combination of stannous chloride and lead acetate is preferably used.

According to the dry process wherein the reaction is carried out in the absence of water, the carboxylic acid, rosin or a derivative thereof is molten under an anhydrous condition together with an oxide of the metal, while eliminating water formed during the reaction. This dry process is called the "fusion method". As a variant of this dry process, the reactants are added to an aromatic hydrophobic solvent such as toluene or xylene and the mixture is heated until the water formed during the reaction is completely eliminated by azeotropic distillation. In either of the cases, the reaction mixture is preferably heated finally up to 220°–230° C. to complete the reaction.

In the composition of this invention, the polymer component to be incorporated with one or more metal salts above mentioned are selected from a wide variety of natural and synthetic polymeric substances, so far as they are non-electroconductive. The use of natural or synthetic rubber or a thermoplastic synthetic resin is preferable. Illustrative of such rubber are, for example, natural rubber, SBR, NBR, CR, IR, IIR and EPT. These rubbers can be used singly or as a mixture of at least two. Examples of the thermoplastic synthetic resin include polyethylene, polypropylene, ethylene-propylene copolymer, polyvinyl chloride, ethylene-vinyl acetate copolymer, SIS, SBS, various polyamides and polyimide. These synthetic resins can also be used singly or as a mixture of at least two or together with the above mentioned rubber.

These rubber and synthetic resins may be incorporated according to a conventional method with a proper amount of one or more auxiliary substances such as a vulcanizer, a vulcanization accelerator, an antioxidant, a stabilizer, a filler, a plasticizer, a pigment and a viscosity imparting or regulating agent. However, one or more of these auxiliary substances should be so selected that these agents may not be reactive with the metal salt used. The selection of these auxiliary substances according to their properties is obvious to those skilled in the art.

The proportion of the metal salt in the composition of this invention is so adjusted that the amount of the metal salt in terms of the metal content is at least 0.1% by weight. If the metal content is less than 0.1% by weight, the amount of the metal will be insufficient to give good conductivity between the laminated circuit substrates. On adjustment of the metal content in the composition in a precise manner, the composition containing a known high content of the metal salt may be diluted on actual use with a proper amount of the polymer component to reduce the content of the metal therein.

The composition of the present invention can be used for imparting electroconductivity to desired spots of the circuit substrates. For this purpose, the composition of this invention is first shaped into a thin film according to any known conventional shaping means such as calendering or extrusion, and the resultant filmy composition is then interposed between the circuit substrates in such a manner that the circuits on both substrates face each other. The laminated circuit substrates with the filmy composition of this invention being interposed therebetween is then subjected to heat treatment at 100°–200° C. for a suitable period of time, usually from several minutes to several hours whereby the laminated substrates are bonded and good conductivity is imparted to spots where the faced metal circuits are closely contacted with each other. The composition of this invention may be applied to circuit substrates in other suitable means. For example, the composition is heated to form a melt which is then applied to circuit substrates by the aid of an applicator or the like means.

By the heat treatment, the polymer component in the composition is softened or molten and bonded to the circuit substrates. In case the polymer is a rubber, it may be vulcanized by the action of a vulcanizer optionally with an accelerator therefor.

The metal salt in the composition, on the other hand, is migrated to the exposed metal areas on the circuit substrates and decomposed there to precipitate the metal whereby the metal areas of the circuits were covered with a film of the precipitated metal. In case the faced metal areas on the laminated circuit substrates are slightly spaced from each other, the precipitated metal is grown on the surface of the metal areas to bridge both metal areas whereby both circuits are electrically conductive in the exposed metal areas.

It is important in the present invention that the metal to be precipitated on the metal in the exposed areas of the laminated circuit substrates should be smaller in ionization tendency than the metal in the exposed areas. In the opposite case wherein the metal in the exposed areas on the substrates is smaller in ionization tendency than the metal of the metal salt, no metal will be precipitated on the metal in the exposed areas of the curcuit substrates. Accordingly, zinc from a salt thereof cannot be precipitated on the metal on the circuit substrates if it is copper or silver. If, for example, a film of a tin-lead soldering alloy is to be formed between the surfaces of copper used as a metal on the laminated circuit substrates to make both circuits electroconductive, a film of the conductive soldering alloy will not be precipitated directly on the surface of the copper. In such a case, however, the formation of the tin-lead conductive film is possible between copper on the circuit substrates by previously subjecting the copper circuit to zinc or aluminum electroplating to form a film of zinc or aluminum on the surface of the copper and then applying the composition of this invention containing stannous and lead salts between the circuit substrates. A similar preliminary electroplating treatment will be necessary if conductivity is created between silver circuit substrates with the composition of this invention containing a copper salt. In case at least two kinds of the metal salts are used, the metals constituting the salt will be precipitated as an alloy.

In the present invention, the mechanism of creating electroconductivity between the metals on the circuit substrates by the formation of bridges of the metal precipitated from the composition of this invention is not clear at present. However, it is surmised to be caused by the following process; At the time of decomposition of the metal salt by heating, the metal on the circuit functions as a catalyst therefor so that the decomposition reaction of the metal salt takes place on the surface of the metal on the circuit and the resultant free metal particles are then dissolved in the metal on the circuit to form an alloy layer. Next, the metal ion formed on the decomposition of the metal salt migrates and is decomposed on the surface of the metal on the circuit on account of the difference in ionization tendency to release the free metal particle which is then deposited on the surface of the initially formed alloy layer eventually to form an electroconductive film and/or bridges of the metal between the surfaces of the metal on the laminated circuit substrates.

The decomposition of the metal salt by heating takes place also in areas somewhat apart from the metal on the circuit whereby the metal particles precipitated from the salt also migrate to the surface of the metal on the circuit and are then integrated with the film and/or bridges already formed thereon to assist the growth of the electroconductive metal film and/or bridges between the laminated circuit substrates. Thus, the film and/or whiskers of the precipitated metal formed on the metal areas of the circuit are grown with the proceeding of the decomposition reaction and the grown film and/or whiskers are integrated together to form electroconductive bridging between the metal surfaces on the laminated circuit substrates.

In order to create good conductivity between the surfaces of metals located on the circuit substrates which are slightly spaced from each other by the composition of this invention being interposed therebetween, the distance between the surfaces of metals is approximately less than several ten $\mu$, although this distance varies more or less according to the sorts of the polymer component and the metal salt, the metal content, and the sort of the metals on the circuits to be treated. In other words, it is necessary to allow a thin layer of the composition of this invention to be present with a thickness of less than several ten $\mu$ between the surfaces of metals located on the circuit.

In case the distance between the surfaces of metals on the circuit is greater than the above mentioned value, the precipitated metal forms whiskers on the surfaces of metals on the circuit but the whiskers extending from both surfaces are not integrated, thus failing to form electroconductive bridgings between the surfaces of metals. In this case, both circuit substrates can be bonded to each other, while keeping them electrically insulated, or in other words, the composition of the present invention functions as a non-conductive binder.

For bonding electronic parts to circuit substrates or binding such circuit substrates in laminated state, the composition of the present invention can be applied onto the circuit substrates or electronic parts according to a method wherein the composition processed to a filmy form is interposed between the circuit substrates placed in such manner that the circuit surfaces having metal areas thereon are faced each other. According to another method, the composition is processed to a hot melt binder by using ethylene-vinyl acetate copolymer, and the binder is then applied in a molten state onto the circuit substrates or electronic parts by the aid of an applicator. As still another method, the composition may conveniently be dissolved in an organic solvent to form a solution or a viscous slurry or latex which is then applied onto the circuit substrates or electronic parts.

The high molecular composition per se of the present invention is non-electroconductive in the normal state and is applicable simply as a binder to circuit substrates and/or electronic parts without making them electrically conductive. In this case, the high molecular composition is present in solid state around the electronic parts and on the circuit substrates to keep them mutually electrically insulated. Circuit substrates and/or electronic parts can be made mutually electroconductive only in the event the surfaces of metals between which the composition of this invention has been interposed is spaced very closely. In this case, electrically conductive metal films and/or whiskers formed on the surfaces of metals grow to form an integrated electroconductive bridge between the surfaces, and the same effect as in soldering the circuit substrates and/or electronic parts can be achieved by the present invention. Thus, the composition of the present invention can be applied onto the total areas of the circuit substrates and/or electronic parts without paying special attention to their complicated circuit patterns to form electrically conductive bridges selectively on the desired spots of the circuit, keeping other areas electrically insulated. This bonding operation is very simple and bonding of the electronic parts and/or circuit substrates can be attained with certainty utilizing plasticity of the polymer component.

In case rubber and/or a soft synthetic resin is used as the polymer component of the composition of this invention, the composition will keep sufficient flexibility even after the circuit substrates are made electroconductive. Accordingly, electroconductivity between the circuits and/or electronic parts is well kept by the flexible composition interposed therebetween unlike the case achieved by the conventional soldering wherein rigid soldered portions may easily be separated off by external force, or alternatively, electroconductivity will become unreliable. In a similar manner, several sheets of circuit panel can be bonded with such flexible composition of this invention to form a multilayer flexible circuit board, thus making it possible to manufacture a highly integrated circuit board.

In the composition of this invention, the metal component is not present as free metal particles but is chemically bound as salt with the organic carboxylic acid, rosin or a derivative thereof. Thus, the composition of this invention free of any free metal particles can form a homogeneous composition with the polymer component and can be applied onto the desired electronic parts without causing any unexpected short circuit due to migration of free metal particles. In view of the aforesaid various advantages, the composition of the present invention is particularly useful in the field of electronic industries.

The present invention will now be illustrated in more detail by way of examples wherein Example 1-27 relate to the preparation of the metal salts.

EXAMPLE 1

In a 200 ml 4-necked flask equipped with a water-separator, a condenser, a thermometer and a stirrer was placed 125 g of naphthenic acid (acid value: 224). After elevating the inner temperature up to 170°-180° C., 10.1 g of stannous oxide and 5.9 g of lead monoxide were added to the acid. After elevating the inner temperature up to 220°-230° C., the mixture were reacted together for 3 hours at the same temperature whereby stannous and lead naphthenates were obtained which had a tin content of 6.3% by weight and a lead content of 3.9% by weight.

EXAMPLE 2

An operation was carried out in the same manner as illustrated in Example 1 except that 90 g of neodecanoic acid as the organic carboxylic acid was used in place of the naphthenic acid used in Example 1, whereby stannous and lead neodecanoates were obtained which had a tin content of 8.4% by weight and a lead content of 5.2% by weight.

EXAMPLE 3

An operation was carried out in the same manner as illustrated in Example 1 except that 142 g of stearic acid as the organic carboxylic acid was used in place of the naphthenic acid used in Example 1, whereby stannous and lead stearates were obtained which had a tin content of 5.6% by weight and a lead content of 3.5% by weight.

EXAMPLE 4

In a 300 ml 4-necked flask equipped with a water-separator, a condenser, a thermometer and a stirrer were placed 122 g of benzoic acid and 40 g of xylene. After elevating the inner temperature up to 120°-130° C. while stirring the mixture, 20.2 g of stannous oxide and 11.8 g of lead monoxide were added to the mixture. After elevating the inner temperature up to 220°-230° C. while eliminating the xylene, the mixture were reacted together for 3 hours at the same temperature whereby stannous and lead benzoates were obtained which had a tin content of 11.6% by weight and a lead content of 7.1% by weight.

EXAMPLE 5

In a 2-liter beaker equipped with a stirrer were placed 125 g of naphthenic acid (acid value: 224), 59 g of a 48% aqueous solution of caustic potash and 1247 g of water. A reaction was carried out for 2 hours at 30° C. with stirring to obtain an aqueous solution of potassium naphthenate having a pH value of 10.5 and containing 10.2% by weight of a solid matter.

On the other hand, 38 g of stannous chloride, 26 g of lead acetate and 200 g of water were charged into a 500 ml beaker equipped with a stirrer and the metal salts were dissolved into the water with stirring. This aqueous solution of the metal salts was added to the aforesaid aqueous solution of potassium naphthenate and a double decomposition reaction was then carried out for 1 hour at 30° C. The reaction mixture was dehydrated, dried and then extracted with toluene. The residue was heated under a reduced pressure of 10 mm Hg to distill off the toluene whereby stannous and lead naphthenates were obtained which had a tin content of 13.2% by weight and a lead content of 9.2% by weight.

EXAMPLE 6

In a 2-liter beaker equipped with a stirrer were placed 141 g of oleic acid (acid value: 198), 59 g of a 48% aqueous solution of caustic potash and 1406 g of water. A reaction was carried out for 2 hours at 30° C. with stirring to obtain an aqueous solution of potassium oleate having a pH value of 10.4 and containing 10.1% by weight of a solid matter.

On the other hand, 38 g of stannous chloride, 26 g of lead acetate and 200 g of water were charged into a 500 ml beaker equipped with a stirrer and the metal salts were dissolved into the water with stirring. This aqueous solution of the metal salts was added to the aforesaid aqueous solution of potassium oleate and a double decomposition reaction was then carried out for 1 hour at 30° C. The reaction mixture was dehydrated, dried and then extracted with toluene. The residue was heated under a reduced pressure of 10 mm Hg to distill off the toluene whereby stannous and lead oleates were obtained which had a tin content of 12.0% by weight and a lead content of 8.4% by weight.

EXAMPLE 7

An operation was carried out in the same manner as illustrated in Example 6 except that 42 g of cupric chloride was used as a metal salt for double decomposition, whereby cupric oleate was obtained which had a copper content of 10.4% by weight.

EXAMPLE 8

An operation was carried out in the same manner as illustrated in Example 6 except that 62.3 g of nickel chloride (6 hydrate) was used as a metal salt for double decomposition, whereby nickel oleate was obtained which had a nickel content of 9.1% by weight.

EXAMPLE 9

An operation was carried out in the same manner as illustrated in Example 6 except that 85 g of silver nitrate was used as a metal salt for double decomposition, whereby silver oleate was obtained which had a silver content of 27.7% by weight.

EXAMPLE 10

In a 2-liter beaker equipped with a stirrer were placed 100 g of phthalic acid, 141 g of a 48% aqueous solution of caustic potash and 1230 g of water. A reaction was carried out for 2 hours at 30° C. with stirring to obtain an aqueous solution of potassium phthalate having a pH value of 10.3 and containing 10.1% by weight of a solid matter.

On the other hand, 215 g of silver nitrate and 200 g of water were charged into a 500 ml beaker equipped with a stirrer and the metal salt was dissolved into the water with stirring. This aqueous solution of silver nitrate was added to the aforesaid aqueous solution of potassium phthalate and a double decomposition reaction was then carried out for 1 hour at 30° C. The reaction mixture was dehydrated, dried and then extracted with toluene. The residue was heated under a reduced pressure of 10 mm Hg to distill off the toluene whereby 225 g of silver phthalate was obtained which had a silver content of 53.5% by weight.

EXAMPLE 11

A reaction was carried out in the same manner as illustrated in Example 10 except that 100 g of isophthalic acid was used in place of the phthalic acid used in Example 10, whereby an aqueous solution of potassium isophthalate having a pH value of 10.2 and containing 10.0% by weight of a solid matter was obtained, which was then subjected to a double decomposition reaction conducted in the same manner as illustrated in Example 10 to obtain 230 g of silver isophthalate having a silver content of 51.5% by weight.

EXAMPLE 12

A mixture of 100 g of sebacic acid, 116 g of a 48% aqueous solution of caustic potash and 1171 g of water was subjected to reaction conducted in the same manner as illustrated in Example 10 to obtain an aqueous solution of potassium sebacate having a pH value of 10.1 and containing 10.1% by weight of a solid matter. To this aqueous solution was added an aqueous solution of 177 g of silver nitrate in 200 g of water to effect a double decomposition reaction in the same manner as illustrated in Example 10 whereby 195 g of silver sebacate was obtained which had a silver content of 49.8% by weight.

EXAMPLE 13

A mixture of 100 g of fumaric acid, 201 g of a 48% aqueous solution of caustic potash and 1370 g of water was subjected to reaction conducted in the same manner as illustrated in Example 10 to obtain an aqueous solution of potassium fumarate having a pH value of 10.5 and containing 10.3% by weight of a solid matter. To this aqueous solution of potassium fumarate was added an aqueous solution of 308 g of silver nitrate in 300 g of water to effect a double decomposition reaction in the same manner as illustrated in Example 10 whereby 275 g of silver fumarate was obtained which had a silver content of 61.3% by weight.

EXAMPLE 14

A mixture of 100 g of trimellitic acid anhydride, 183 g of a 48% aqueous solution of caustic potash and 1330 g of water was subjected to reaction conducted in the same manner as illustrated in Example 10 to obtain an aqueous solution of potassium salt of trimellitic acid anhydride having a pH value of 10.2 and containing 10.1% by weight of a solid matter. To this aqueous solution was added an aqueous solution of 279 g of silver nitrate in 270 g of water to effect a double decomposition reaction in the same manner as illustrated in Example 10 whereby 246 g of silver salt of trimellitic acid anhydride was obtained which had a silver content of 57.5% by weight.

EXAMPLE 15

A mixture of 100 g of pyromellitic anhydride, 214 g of a 48% aqueous solution of caustic potash and 1400 g of water was subjected to reaction conducted in the same manner as illustrated in Example 10 to obtain an aqueous solution of potassium salt of pyromellitic acid having a pH value of 10.4 and containing 10.0% by weight of a solid matter. To this aqueous solution was added an aqueous solution of 328 g of silver nitrate in 300 g of water to effect a double decomposition reaction in the same manner as illustrated in Example 10 whereby 265 g of silver salt of pyromellitic acid was obtained which had a silver content of 59.8% by weight.

EXAMPLE 16

In a 200 ml 4-necked flask equipped with a water-separator, a condenser, a thermometer and a stirrer was placed 100 g of oleic acid. After elevating the inner temperature up to 170°-180° C., 3.7 g of stannous oxide and 2.4 g of lead monoxide were added to the acid. After elevating the inner temperature up to 220°-230° C., the mixture were reacted together for 3 hours at the same temperature whereby stannous and lead oleates were obtained which had a tin content of 2.9% by weight and a lead content of 1.8% by weight.

EXAMPLE 17

An operation was carried out in the same manner as illustrated in Example 16 except that the amounts of the stannous oxide and lead monoxide used in Example 16 were 0.8 g and 0.5 g, respectively, whereby stannous and lead oleates were obtained which had a tin content of 0.61% by weight and a lead content of 0.39% by weight.

EXAMPLE 18

In a 1 liter 4-necked flask equipped with a condenser and a stirrer were placed 175 g of a gum rosin produced in China (acid value: 169; tint: grade X; softening point: 78° C.), 63 g of a 48% aqueous solution of caustic potash and 374 g of water. A reaction of the mixture was carried out for 3 hours at 90° C. with stirring to obtain an aqueous solution of potassium salt of the gum rosin having a pH value of 10.5 and containing 30.5% of a solid matter.

A 2 liter beaker equipped with a stirrer was charged with 600 g of the aqueous solution of the potassium salt of the gum rosin obtained in the preceding step and 850 g of water to dilute the aqueous solution under agitation. On the other hand, 38 g of stannous chloride, 26 g of lead acetate and 200 g of water were charged into a 500 ml beaker equipped with a stirrer and the metal salts were dissolved in the water with stirring. This aqueous solution of the metal salts was added to the aforesaid diluted aqueous solution of potassium salt of the gum rosin, and a double decomposition reaction was then carried out for 1 hour at 30° C. The reaction mixture was dehydrated and dried to obtain stannous and lead salts of the gum rosin having a tin content of 9% by weight and a lead content of 5.8% by weight.

EXAMPLE 19

An operation was carried out in the same manner as illustrated in Example 18 except that 84 g of silver nitrate was used in place of stannous chloride and lead acetate as metal satls for double decomposition, whereby silver salt of the gum rosin was obtained which had a silver content of 21% by weight.

EXAMPLE 20

An operation was carried out in the same manner as illustrated in Example 18 except that 42 g of cupric chloride was used in place of stannous chloride and lead acetate in case of double decomposition, whereby cupric salt of the gum rosin was obtained which had a copper content of 14% by weight.

EXAMPLE 21

An operation was carried out in the same manner as illustrated in Example 18 except that tall oil rosin (acid value: 168.5; tint: grade X; softening point: 76° C.) was used in place the gum rosin produced in China, whereby stannous and lead salts of the tall oil rosin were obtained which had a tin content of 8.8% by weight and a lead content of 5.8% by weight.

EXAMPLE 22

An operation was carried out in the same manner as illustrated in Example 18 except that disproportioned rosin (acid value: 167.0; tint: grade WG; softening point: 68° C.) was used in place of the gum rosin produced in China, whereby stannous and lead salts of the asymmetric rosin was obtained which had a tin content of 8.5% by weight and a lead content of 5.5% by weight.

EXAMPLE 23

In a 500 ml 4-necked flask equipped with a condenser, a water-separator, a thermometer and a stirrer was placed 300 g of tall oil rosin (acid value: 168; tint: grade X; softening point: 76° C.). The flask was heated with stirring on a mantle heater to melt the rosin. The molten rosin was once cooled down to 180° C., admixed with 57 g of maleic anhydride. The mixture was heated for 2 hours at 190°–200° C. to effect a maleic anhydride-addition reaction whereby 350 g of a maleic anhydride-adduct of the rosin was obtained which had an acid value of 324.

In a 1 liter 4-necked flask equipped with a condenser and a stirrer were placed 175 g of the maleic anhydride-adduct of the rosin obtained in the preceding step, 120 g of a 48% aqueous solution of caustic potash and 318 g of water. A reaction of the mixture was carried out for 3 hours at 90° C. with stirring to obtain an aqueous solution of potassium salt of the maleic anhydride-adduct of rosin having a pH value of 10.3 and containing 30% of a solid matter.

A 2 liter beaker equipped with a stirrer is charged with 600 g of the aqueous solution of the potassium salt of the maleic anhydride-adduct of the rosin obtained in the preceding step and 850 g of water to dilute the aqueous solution under agitation. On the other hand, 69 g of stannous chloride, 45 g of lead acetate and 200 g of water were charged into a 500 ml beaker equipped with a stirrer and the metal salts were dissolved in the water with stirring. This aqueous solution of the metal salts was added to the aforesaid diluted aqueous solution of potassium salt of the maleic anhydride-adduct of the rosin, and a double decomposition reaction was then carried out for 1 hour at 30° C. The reaction mixture was dehydrated and dried to obtain stannous and lead salts of the maleic anhydride-adduct of the rosin having a tin content of 17% by weight and a lead content of 12% by weight.

EXAMPLE 24

In a 500 ml 4-necked flask equipped with a condenser, a water-separator, a thermometer and a stirred was placed 300 g of tall oil rosin (acid value: 168; tint: grade X; softening point: 76° C.). The flask was heated with stirring on a mantle heater to melt the rosin. The molten rosin was once cooled down to 180° C., admixed with 24 g of fumaric acid. The mixture was heated for 2 hours at 190°–200° C. to effect a fumaric acid-addition reaction whereby 320 g of a fumaric acid-adduct of the rosin was obtained which had a neutralization value of 226.

In a 1 liter 4-necked flask equipped with a condenser and a stirred were placed 175 g of the fumaric acid-adduct of the rosin obtained in the preceding step, 83 g of a 48% aqueous solution of caustic potash and 417 g of water. A reaction of the mixture was carried out for 3 hours at 90° C. with stirring to obtain an aqueous solution of potassium salt of the fumaric acid-adduct of the rosin having a pH value of 10.3 and containing 30% of a solid matter.

A 2 liter beaker equipped with a stirrer is charged with 600 g of the aqueous solution of the potassium salt of the fumaric acid-adduct of the rosin obtained in the preceding step and 850 g of water to dilute the aqueous solution under agitation. On the other hand, 43 g of stannous chloride, 28 g of lead acetate and 200 g of water were charged into a 500 ml beaker equipped with a stirrer and the metal salts were dissoloved in the water with stirring. This aqueous solution of the metal salts was added to the aforesaid diluted aqueous solution of potassium salt of the fumaric acid-adduct of the rosin, and a double decomposition reaction was then carried out for 1 hour at 30° C. The reaction mixture was dehydrated and dried to obtain stannous and lead salts of the fumaric acid-adduct of the rosin having a tin content of 13% by weight and a lead content of 9% by weight.

EXAMPLE 25

In a 1 liter 4-necked flask equipped with a water-separator, a condenser, a thermometer and a stirrer was placed 300 g of a gum rosin produced in China (previously described). The flask was heated to melt the rosin at 220°–230° C. while eliminating water. To the melt were added 20.3 g of stannous oxide and 13.0 g of lead monoxide, and the mixture was reacted together for 3 hours at the same temperature whereby stannous and lead salts of the gum rosin were obtained which had a tin content of 5.5% by weight and a lead content of 3.8% by weight.

EXAMPLE 26

An operation was carried out in the same manner as illustrated in Example 25 except that the amounts of stannous oxide and lead monoxide used in Example 25 were 10.0 g and 6.5 g, respectively, whereby stannous and lead salts of the gum rosin was obtained which had a tin content of 2.8% by weight and a lead content of 1.8% by weight.

EXAMPLE 27

An operation was carried out in the same manner as illustrated in Example 25 except that the amounts of stannous oxide and lead monoxide used in Example 25 were 0.55 g and 0.4 g, respectively, whereby stannous and lead salts of the gum rosin was obtained which had a tin content of 0.55% by weight and a lead content of 0.4% by weight.

The following example illustrates a process for preparing conductive high molecular compositions of the present invention, using the metal salts of the organic carboxylic acids or rosin or derivatives thereof obtained in the foregoing Examples 1–27, and also shows a result of tests made for measuring conductivity between circuit substrates bonded with the compositions.

EXAMPLE 28

(1) Preparation of a Conductive High Molecular Composition

The conductive high molecular compositions were prepared according to a process as described hereinafter, using the metal salts of the organic carboxylic acids, rosin and derivatives thereof, together with natural rubber, SBR, atactic polypropylene and ethylene-vinyl acetate copolymer as polymer components.

In case of using natural rubber as the polymer component, a 200 ml 4-necked flask equipped with an Allihn condenser, a thermometer and a stirrer was charged with 90 g of toluene, 10 g of a smoked sheet #3 and any one of the metal salts synthesized in the foregoing Examples 1–27. The mixture was stirred for 5 hours under reflux of the toluene whereby the metal salt and the rubber were dissolved to form a solution as a test sample.

In case of using SBR as the polymer component, the operation was carried out in the same manner as described with respect to the case of using the natural rubber except that SBR #1500 was used in place of the smoked sheet #3, whereby a similar solution was obtained as a test sample.

In case of using atactic polypropylene as the polymer component, any one of the metal salts synthesized in the foregoing examples was mixed with atactic polypropylene (manufactured by Mitsui-Toatsu KK, Japan) and the mixture was molten to prepare a test sample.

In case of using an ethylene-vinyl acetate copolymer as the polymer component, any one of the metal salts synthesized in the foregoing examples was mixed with 100 g of an ethylene-vinyl acetate copolymer (Everflex #220, Mitsui Polychem. KK, Japan) and 50 g of paraffin wax (m.p. 66°–68° C.), and the mixture was molten at 180° C. to prepare a test sample.

The amount of the metal salt incorporated into the composition was so adjusted that the content of the metal component in the solid matter might be about 1.0% by weight. In case of Examples 16 and 17, however, the content of the metal component in the solid matter was adjusted to 0.2% by weight and 0.05% by weight, respectively. In case of Example 27, the contents of the metals were adjusted to 0.2% by weight and 0.05% by weight.

(2) Bonding of Substrates Having a Metal Film Thereon

A commercially available throughhole substrate (land pitch: 2.54 mm; land 2 mm in total) as a material to be bonded was cut into pieces of 50 mm square and 2 pieces among them were used for the test. A resist was applied on the surface of the throughhole substrate whereby the overall surface became even with the surface of the land. The surface of the land was then subjected to non-electrolytic nickel plating whereby a nickel film (thickness: 1μ) was plated on the surface of the land.

The test sample of the conductive high molecular composition prepared in the preceding step (1) was then applied by the aid of an applicator onto the surface of one of the throughhole substrates in such manner that the thickness of a solid matter applied might be 50μ. This throughhole substrate was laminated with the other in such manner that the lands on both substrates faced each other, and the laminated substrates were then heated for 15 minutes at 250° C.

(3) Measurement of Electric Resistance

Electric resistance between the lands of the bonded throughhole substrates facing each other was measured in a conventional manner before and after the heating. Electric resistance between the adjacent land on each throughhole substrate was also measured after the heating.

(4) Result of the Test

A result of the test is shown in Tables 1 and 2. The abbreviations used in these tables have the following meanings:

| Abbreviations | Meanings |
| --- | --- |
| Resist b/h | Resistance before heating |
| Resist a/h | Resistance after heating |
| NR | Natural rubber |
| APP | Atactic polypropylene |
| EVA | Ethylene-vinyl acetate copolymer |

TABLE 1

| Electric Resistance ($\Omega \cdot cm$) | Example No. | Metal salts of organic carboxylic acids | | | | Polymer components | | | |
|---|---|---|---|---|---|---|---|---|---|
| | | Acids | Metals | Method for synthesis | Content of metals | NR | SBR | APP | EVA |
| Resist b/h | | | | | | $1 \times 10^{14}$ | $1 \times 10^{15}$ | $1 \times 10^{16}$ | $1 \times 10^{14}$ |
| | 1 | Naphthenic acid | Sn, Pb | Dry | 1(%) | $7.5 \times 10^{-6}$ | $7.2 \times 10^{-6}$ | $8.2 \times 10^{-6}$ | $7.2 \times 10^{-6}$ |
| | 2 | Neodecanoic acid | " | " | 1 | $7.6 \times 10^{-6}$ | $6.9 \times 10^{-6}$ | $7.8 \times 10^{-6}$ | $7.4 \times 10^{-6}$ |
| | 3 | Stearic acid | " | " | 1 | $6.9 \times 10^{-6}$ | $7.4 \times 10^{-6}$ | $8.0 \times 10^{-6}$ | $6.5 \times 10^{-6}$ |
| | 4 | Benzoic acid | " | " | 1 | $7.8 \times 10^{-6}$ | $7.7 \times 10^{-6}$ | $8.2 \times 10^{-6}$ | $6.8 \times 10^{-6}$ |
| | 5 | Naphthenic acid | " | Wet | 1 | $6.4 \times 10^{-6}$ | $6.8 \times 10^{-6}$ | $7.7 \times 10^{-6}$ | $7.4 \times 10^{-6}$ |
| | 6 | Oleic acid | " | " | 1 | $7.8 \times 10^{-6}$ | $7.3 \times 10^{-6}$ | $7.9 \times 10^{-6}$ | $7.2 \times 10^{-6}$ |
| | 7 | " | Cu | " | 1 | $7.3 \times 10^{-6}$ | $7.5 \times 10^{-6}$ | $8.2 \times 10^{-6}$ | $6.9 \times 10^{-6}$ |
| Resist a/h | 8 | " | Ni | " | 1 | — | — | — | — |
| | 9 | " | Ag | " | 1 | $5.2 \times 10^{-6}$ | $5.5 \times 10^{-6}$ | $6.7 \times 10^{-6}$ | $5.3 \times 10^{-6}$ |
| | 10 | Phthalic acid | " | " | 1 | $5.1 \times 10^{-6}$ | $4.5 \times 10^{-6}$ | $6.3 \times 10^{-6}$ | $4.7 \times 10^{-6}$ |
| | 11 | Isophthalic acid | " | " | 1 | $5.5 \times 10^{-6}$ | $5.8 \times 10^{-6}$ | $6.5 \times 10^{-6}$ | $5.2 \times 10^{-6}$ |
| | 12 | Sebacic acid | " | " | 1 | $5.4 \times 10^{-6}$ | $5.6 \times 10^{-6}$ | $6.2 \times 10^{-6}$ | $5.4 \times 10^{-6}$ |
| | 13 | Fumaric acid | " | " | 1 | $5.4 \times 10^{-6}$ | $5.4 \times 10^{-6}$ | $6.5 \times 10^{-6}$ | $5.3 \times 10^{-6}$ |
| | 14 | Trimellitic acid | " | " | 1 | $5.2 \times 10^{-6}$ | $5.5 \times 10^{-6}$ | $6.5 \times 10^{-6}$ | $4.9 \times 10^{-6}$ |
| | 15 | Pyromellitic acid | " | " | 1 | $5.4 \times 10^{-6}$ | $5.3 \times 10^{-6}$ | $6.3 \times 10^{-6}$ | $4.8 \times 10^{-6}$ |
| | 16 | Oleic acid | Sn, Pb | Dry | 0.2 | $1440 \times 10^{-6}$ | $1560 \times 10^{-6}$ | $2130 \times 10^{-6}$ | $1510 \times 10^{-6}$ |
| | 17 | " | " | " | 0.05 | 1.9 | 2.2 | 3.3 | 1.8 |

TABLE 2

| Electric Resistance ($\Omega \cdot cm$) | Example No. | Metal salts of rosin or derivatives thereof | | | | Polymer components | | | |
|---|---|---|---|---|---|---|---|---|---|
| | | Sort of rosin | Metals | Method for synthesis | Content of metals | NR | SBR | APP | EVA |
| Resist b/h | | | | | | $1 \times 10^{14}$ | $1 \times 10^{15}$ | $1 \times 10^{16}$ | $1 \times 10^{14}$ |
| | 18 | Gum rosin | Sn, Pb | Wet | 1.0 | $7.6 \times 10^{-6}$ | $7.5 \times 10^{-6}$ | $7.8 \times 10^{-6}$ | $7.8 \times 10^{-6}$ |
| | 19 | " | Ag | " | 1.0 | $6.4 \times 10^{-6}$ | $6.4 \times 10^{-6}$ | $6.4 \times 10^{-6}$ | $6.4 \times 10^{-6}$ |
| | 20 | " | Cu | " | 1.0 | $7.6 \times 10^{-6}$ | $7.5 \times 10^{-6}$ | $7.7 \times 10^{-6}$ | $7.8 \times 10^{-6}$ |
| | 21 | Tall oil rosin | Sn, Pb | " | 1.0 | $7.6 \times 10^{-6}$ | $7.7 \times 10^{-6}$ | $7.8 \times 10^{-6}$ | |
| | 22 | Asymmetric rosin | " | " | 1.0 | $7.9 \times 10^{-6}$ | $7.8 \times 10^{-6}$ | $7.7 \times 10^{-6}$ | $7.7 \times 10^{-6}$ |
| Resist a/h | 23 | Maleic anhydride adduct | " | " | 1.0 | $7.6 \times 10^{-6}$ | $7.5 \times 10^{-6}$ | — | — |
| | 24 | Fumaric acid adduct | " | " | 1.0 | — | — | — | — |
| | 25 | Gum rosin | " | Dry | 1.0 | $12.3 \times 10^{-6}$ | $12.3 \times 10^{-6}$ | $12.5 \times 10^{-6}$ | $12.5 \times 10^{-6}$ |
| | 26 | " | " | " | 1.0 | $251 \times 10^{-6}$ | $254 \times 10^{-6}$ | $250 \times 10^{-6}$ | $263 \times 10^{-6}$ |
| | 27 | " | " | " | 0.2 | $1560 \times 10^{-6}$ | $1600 \times 10^{-6}$ | $1630 \times 10^{-6}$ | $1650 \times 10^{-6}$ |
| | | | | | 0.05 | 2.0 | 2.1 | 2.0 | 2.5 |

As for the electric resistance between the lands facing each other before heating, the value varied according to the sort of the polymer component but no significant difference in electric resistance was found according to the sort of the metal salt. In Tables 1 and 2, therefore, an average value was given for each polymer component with respect to the electric resistance between the lands facing each other. Since no difference was found in electric resistance between the adjacent lands on each substrate before and after the heating, such electric resistance values in case of the adjacent lands were omitted in Tables 1 and 2.

The following facts are apparently revealed from the results described above and shown in Tables 1 and 2:

(a) The conductive high molecular composition per se of the present invention has no electroconductive property at normal state and functions as an insulating material. This is evident from a high electric resistance before the heating between the opposite lands of the laminated substrates between which the composition has been interposed.

(b) By heating the laminated substrates, electroconductivity is created only between the opposite lands of the laminated substrates as seen from the electric resistance values after heating which are significantly decreased from the values before heating. However, the adjacent land on each substrate is kept insulated. This apparently shows that electroconductivity is created only between the metal films.

(c) In case the content of the metal component in the composition is as small as 0.05% by weight, the created electroconductivity is not so remarkable.

The composition of the present invention thus shows a quite different dual function as an insulating material in a place where the property of insulators is required and as an electroconductive material in a place where the property of an electroconductor is required. The composition of the present invention is thus very useful in the field of electric and electronic industries as having the two opposite properties of insulators and conductors.

It is understood that the preceding representative examples may be varied within the scope of the present specification both as to the sorts of the metal salts and the polymer components and the treating conditions by those skilled in the art to achieve essentially the same results.

As many widely different embodiments of this invention may be made without departing from the spirit and scope thereof, it is to be construed that this invention is not limited to the specific embodiments thereof except as defined in the appended claims.

What is claimed is:

1. An electroconductive high molecular weight composition for coating a substrate containing a metal, said composition consisting essentially of a non-conductive polymer component having a metal salt of an acid substance selected from the group consisting of an aromatic organic carboxylic acid, rosin and a rosin derivative incorporated therein and wherein the metal salt of said acid substance is smaller in ionization tendency than said metal in said substrate.

2. The composition according to claim 1, wherein the organic carboxylic acid is an aromatic mono- or di-carboxylic acid.

3. The composition according to claim 1, wherein the rosin derivative is selected from disproportioned rosin, hydrogenated rosin, gum rosin, tall oil rosin, wood rosin, maleic acid-adduct of rosin and fumaric acid-adduct of rosin.

4. The composition according to claim 1, wherein the metal content in the composition is at least 0.1% by weight.

5. The composition according to claim 1, wherein the polymer component is natural or synthetic rubber and/or a thermo-plastic synthetic resin.

* * * * *